US006806046B2

(12) United States Patent
Johnston-Dow et al.

(10) Patent No.: US 6,806,046 B2
(45) Date of Patent: Oct. 19, 2004

(54) METHODS FOR HIV SEQUENCING AND GENOTYPING

(75) Inventors: Leslie A. Johnston-Dow, Palo Alto, CA (US); Lisa Demeter, Rochester, NY (US); Camille B. White, San Diego, CA (US); Keming Song, Chesterfield, MO (US); Robert Kohlenberger, Burlingame, CA (US); Morgan Conrad, Montara, CA (US); Angela Myers, Alameda, CA (US)

(73) Assignee: Applera Corporation, Foster City, CA (US)

( * ) Notice: Subject to any disclaimer, the term of this patent is extended or adjusted under 35 U.S.C. 154(b) by 83 days.

(21) Appl. No.: 10/335,059

(22) Filed: Dec. 31, 2002

(65) Prior Publication Data

US 2003/0219725 A1 Nov. 27, 2003

(Under 37 CFR 1.47)

Related U.S. Application Data

(63) Continuation of application No. 10/092,022, filed on Mar. 5, 2002, now Pat. No. 6,531,588, which is a continuation of application No. 09/158,695, filed on Sep. 21, 1998, now Pat. No. 6,379,957.

(51) Int. Cl.[7] ............................. C12Q 1/70; C12Q 1/68; C12Q 1/06
(52) U.S. Cl. ................................. 435/5; 435/6; 435/39
(58) Field of Search .................................. 435/5, 6, 39

(56) References Cited

U.S. PATENT DOCUMENTS 5,800,996 A  9/1998  Lee et al.

OTHER PUBLICATIONS

Brown and Richman, *Nature Medicine*, 3:268–271(1997).
Coffin, *Science*, 267:483–489 (1995).
Colimon et al., *J. Virological Methods*, 58:7–19 (1996).
Condra et al., *J. of Virology*, 70:8270–8276 (1996).
Condra et al., *Nature*, 374:569–571 (1995).
Conrad, Abstract, *Human Immunology*, 44, Suppl, No. 7.4 (No. 217) (1995).
Edelstein et al., *J. Clinical Microbiology*, p. 569–572 (1998).
Hirsch et al., *J. Amer. Med. Assn.*, 279:1984–1991 (1998).
Larder et al., *Nature*, 365:451–453 (1993).
Manksy and Temin, *J. of Virology*, 69:5087–5094 (1995).
Mayers, *J. Amer. Med. Assn.*, 279:2000–2002 (1998).
Molla et al., *Nature Medicine*, 2:760–766 (1996).
Seillier–Moiseiwitsch et al., *Annu. Rev. Genet.*, 28:559–596 (1994).
Wain–Hobson, *Current Opinions in Genetics and Development*, 3:878–883 (1993).
Wainberg and Friedland, *J. Amer. Med. Assn.*, 279:1977–1983 (1998).

*Primary Examiner*—Hankyel T. Park
(74) *Attorney, Agent, or Firm*—Finnegan, Henderson, Farabow, Garrett & Dunner, L.L.P.

(57) ABSTRACT

Methods are provided for amplifying regions of the HIV pol gene amplifying double-stranded nucleic acid template derived from HIV tube RT-PCR with novel PCR primers to produce amplified target sequences. Methods are also provided for analyzing the nucleotide sequence of these amplified targets using novel sequencing primers and the data is analyzed. The determined nucleotide sequence can be compared to the sequence of known drug resistance mutations in the HIV pol gene to determine the viral genotype.

8 Claims, No Drawings

METHODS FOR HIV SEQUENCING AND GENOTYPING

This application is a continuation of application Ser. No. 10/092,022, filed Mar. 5, 2000, now U.S. Pat. No. 6,531,588 which is a continuation of application Ser. No. 09/158,695, filed Sep. 21, 1998, now U.S. Pat. No. 6,379,957 B1. U.S. application Ser. Nos. 09/158,695 and 10/092,022 are incorporated by reference herein in their entirety.

BACKGROUND AND SUMMARY OF THE INVENTION

The present invention relates to methods for sequencing the Human Immunodeficiency Virus (HIV) nucleic acids. More specifically, the present invention relates to methods for obtaining information on the genetic sequences of HIV nucleic acid from a patient. That information can be used to genotype a HIV quasi-species present in the patient.

The detection of mutations conferring drug resistance in the HIV pol gene is significant in determining drug sensitivity of the virus. During the course of treatment of a disease, the infectious microorganism or virus, such as HIV, can become resistant due to a loss of sensitivity to the particular drug in use, which generally results in spread of the disease and increased morbidity. At the genetic level, important changes can occur within the virus in response to drug therapy. Specific changes in a nucleic sequence or nucleic acid sequences of the virus that correlate with drug resistance are defined as drug resistance mutations. The nucleic sequences may be target nucleic acid sequences that are affected by a drug or therapeutic agent. Such target nucleic acids may encode a viral protein, such as an enzyme.

Due to the emergence of drug resistance mutations, one should obtain information concerning the genetic sequence of target nucleic acids of the virus in the patient for proper diagnosis and for choosing an appropriate treatment. Once this information is obtained, failure of drug therapy can be monitored at the genetic level rather than waiting for the re-emergence or worsening of clinical symptoms. This may be accomplished by isolating the nucleic acid for the infectious organism (virus) from the patient, determining the sequence of the target nucleic acids of the organism, and identifying mutations known to confer drug resistance.

This approach can also be used to intelligently prescribe effective drug treatment. The nucleic acid sequence of the organism's target nucleic acids can be obtained from the patient prior to treatment, and the organism's resistance to a particular drug can be determined.

One way to obtain de novo sequence information for the target nucleic acids of an HIV quasi-species present in a patient is to obtain a sample of the patient's plasma or tissue. The viral RNA or DNA from that sample is then extracted. If the genetic information is RNA, it should typically be reverse-transcribed into DNA. The DNA of the HIV target nucleic acid is then amplified by PCR, and the PCR products are sequenced. This sequence data can then be compared to a reference sequence for HIV and with all known drug resistance mutations.

Many RNA containing viruses, including HIV, rapidly mutate even in the absence of drug therapy. This is due to the lack of fidelity and proof-reading functions by the virus's RNA polymerase or reverse transcriptase for retroviruses. For HIV reverse transcriptase, for example, the estimated spontaneous mutation rate is $3\times10^{-5}$ nucleotides per replication cycle (Mansky and Temin, J. Virol., 69:5087–94, 1995).

The frequent use of antiviral drugs in the treatment of HIV infection has led to the development of drug resistance in AIDS patients. In the case of HIV, it the genetic sequence of the HIV pol gene (which encodes the viral protease and reverse transcriptase) is often the target nucleic acid (Wainberg and Friedland, J. Am. Med. Assn., 279:1977–93, 1998). Drug resistant HIV mutants have been isolated from infected individuals. The present inventors believe that a 1.57 kilobase (kb) region of the pol gene is a particularly important region containing clinically relevant mutations.

The high degree of enzyme-induced genetic variability, in addition to the selective pressures of drug therapy, makes genotypic assessment of HIV very complex. Typically, HIV infected individuals harbor multiple viral genotypes or quasi-species, whether due to random enzyme-induced mutations, drug resistance-related mutations, or a combination of such mutations. As drug resistant mutant HIV strains become more prevalent, individuals with no history of drug treatment are becoming infected with drug resistant viruses.

Presently, determining appropriate treatment of HIV infections does not typically involve genetic analysis of the HIV pol gene (protease and reverse transcriptase) from patient plasma HIV RNA. Thus, physicians typically can only diagnose drug resistance in a patient if the patient fails to respond to therapy. Moreover, without genetic analysis, if a patient is failing therapy, it is difficult, if not impossible, to determine for which drugs the patient is still sensitive. By isolating, amplifying, and sequencing the patient's HIV pol gene from plasma, it will be possible to determine the number of drug resistance mutations and tailor further therapy accordingly.

Consequently, there exists a need for rapid, reliable methods for obtaining the de novo nucleic acid sequences from clinical samples from patients who are, or may be, infected with HIV. In addition to providing patient-specific genotype information for use in identifying an appropriate treatment and monitoring drug resistance, the public health community would benefit from rapid, standardized, and reliable sequence information to establish the significance and relevance of drug-associated resistance mutations.

Current HIV genotyping procedures include hybridization based assays using labeled oligonucleotide probes and "home brew" (internally created) sequencing based assays. Because of a high rate of mutation in HIV, technologies using labeled oligonucleotides to represent "mutant" or "wild-type" forms at a particular codon of the gene sequence will be adversely affected. For example, mutations which are not associated with drug resistance will frequently occur, and may affect the binding of either "wild-type" or "mutant" probes, giving an anomalous result. Therefore, de novo sequencing should be a more accurate way to represent genetic changes of these highly variable sequences. This is especially important for organisms such as HIV because of the inherent genetic variability due to the lack of proofreading activity of HIV reverse transcriptase. Since the understanding of HIV mutations and their association with drug resistance is continually being elucidated, obtaining the de novo sequence of the HIV pol gene from patient populations undergoing drug therapy is important in establishing the clinical relevance of drug resistance in HIV.

Although a variety of home brew sequencing based assays have been used in individual research labs, the present inventors are not aware of comprehensive, commercially available systems for determining the de novo sequence of infectious organisms. The general poor quality and lack of proper controls, seen with most home brew assays, have hindered generation of accurate data which are crucial for studying drug resistance.

Other HIV genotyping procedures involve polymerase chain reaction (PCR) using nested primers to amplify HIV nucleic acid sequences. The nested primer procedure typically requires a different set of primers for each PCR cycle, with each successive set of primers being selected to anneal within the fragment amplified by the prior PCR cycle. While this procedure is effective at amplifying a known sequence present at low copy number, the use of multiple sets of primers, each of which must hybridize successively to a target sequence in the gene of interest, can result in a loss of the ability to amplify highly variable nucleic acid sequences. This would occur, for example, where a mutation was located in any of the target sequences in a region where primers are designed to hybridize. This results in biased selection of HIV quasi-species wherein significant drug resistance mutations may remain entirely undetected until drug failure occurs in the patient.

One goal of HIV genotyping is to monitoring drug resistance at the genetic level by identifying as many different HIV quasi-species as possible. Among such quasi-species, there are likely to be mutations due to drug resistance as well as random mutations due to polymerase error in the virus population. The number of HIV quasi-species detectable by the genotyping assay should be maximized. Therefore, a need also exists for genotyping procedures which detects many different HIV quasi-species from a rapidly mutating virus population.

An object of the invention is to provide methods for obtaining de novo sequence information for different HIV quasi-species present in patient's samples. This invention will allow effective diagnosis and treatment for patients and will also provide methods for monitoring drug therapy failures at the genetic level. Another object of the instant invention is to provide a standardized assay which will allow for rapid and accurate identification of mutations associated with drug resistance.

According to certain preferred embodiments, the inventors have achieved improved sensitivity and determined a greater number of HIV quasi-species than procedures that employ nested primers. Certain embodiments involve a stream-lined assay, including a single-tube two step amplification procedure, coupled with automated sequence analysis and correlation with known drug resistance mutations. Such embodiments provide rapid, reliable assays that have acceptable sensitivity and specificity.

Additional objects and advantages of the invention will be set forth in part in the description which follows, and in part will be apparent from the description, or may be learned by practice of the invention.

According to certain embodiments, the invention comprises methods for amplifying a target nucleic sequence of HIV including combining a double-stranded nucleic acid template derived from HIV with certain specific PCR primers, a temperature-stable DNA polymerase, and deoxyribonucleotides, and amplifying the template to produce amplified target sequences. Certain embodiments include analysis of the amplified sequences. In certain embodiments, target sequence analysis is accomplished using a computer program which determines target gene sequences and, then compares those sequences with HIV reference sequences and a table of known drug resistance mutations.

In other embodiments, the invention comprises methods for sequencing HIV nucleic acid including combining a double-stranded nucleic acid template derived from HIV and one or more specific sequencing primers, amplifying the HIV derived double-stranded nucleic acid template to produce amplified sequencing products, separating those amplified sequencing products to obtain nucleic acid sequence data, and analyzing the nucleic acid sequencing data.

In yet other embodiments of the present invention, target nucleic acid sequencing involves use of particular dye-terminator chemistry. Such chemistry is useful for automated sequence analysis and determination of heterozygosity at a given nucleotide.

It is to be understood that both the foregoing general description and the following detailed description are exemplary and explanatory only and are not restrictive of the invention, as claimed.

DESCRIPTION OF PREFERRED EMBODIMENTS

The references discussed or cited in this application are all specifically incorporated by reference into this application.

For use in the present invention, typically, samples from infected or potentially infected patients are used as a source of HIV. Tissue samples or body fluid samples can be used. As used herein, body fluids include, but are not limited to, whole blood, plasma, serum, peripheral blood mononuclear cells (PBMC), other fractionated blood products, tears, saliva, semen, vaginal secretions, serous and pleural cavity fluids, washes from various mucous membranes such as the eye, nose or throat, and the like. Plasma, which may be obtained by methods well known in the art, is exemplary of a preferred source of proviral nucleic acid and will be used in the following examples.

According to certain embodiments, plasma samples, which may be frozen prior to use, are centrifuged under conditions that results in pelleting of the virion from the sample. After discarding the supernatant, the virus is lysed with lysis buffer. A particular buffer that may be used includes 4 M guanidine thiocyanate, 25 mM sodium citrate, 0.5% sodium lauroyl sarcosine, 100 mM dithiothreitol, 80 µg/ml glycogen in sterile water. Viral RNA can be precipitated using absolute isopropanol and can be pelleted by centrifugation. The resulting supernatant is discarded and the pellet is washed and again pelleted by centrifugation. The wash solution can include 70% ethanol. HIV RNA samples are resuspended in an RNA diluent. According to certain embodiments, such a diluent can include 10 ng/ml polyrA from Pharmacia in RNase-free water. All steps can be performed using prechilled instruments and buffers, and the samples can be maintained at 4° C. or stored at −70° C.

Double stranded DNA template is then created from the prepared HIV RNA. According to certain embodiments, random hexamers are used as primers at the 3' end in conjunction with a reverse transcriptase (RT) procedure. An advantage of using random hexamers is that sequence variability will not affect cDNA generation. Random hexamers may also stabilize RNA secondary structure, which is known to be quite significant in HIV pol RNA. Appropriate conditions are used that result in cDNA generation from purified HIV RNA. In certain preferred embodiments, the double stranded templates produced in the RT reaction are then amplified in a PCR amplification method.

Certain embodiments of the present invention also involve sequencing particular regions of HIV pol. The present inventors targeted various regions of HIV pol, including particular 1.57 kb and 2.1 kb regions. To attempt to locate mutations located at the 3' end of HIV pol, primers were designed and tested to amplify a 2.1 kb region containing the entire coding region of protease and reverse transcriptase enzymes from HIV pol. This assay will be used to amplify and sequence the AIDS Clinical Testing Group (ACTG) 320 study, which will document the mutation patterns and clinical relevance of mutations in HIV pol in response to multi-drug therapy (protease and reverse transcriptase inhibitors). In addition to the 1.57 kb region, an additional 3' RT region (approximately 0.7 kb) was targeted for amplification and sequencing. These two amplification and sequencing protocols cover the entire 2.1 kb of HIV protease and reverse transcriptase for the ACTG 320 study.

Novel PCR primers were developed and used to amplify the 0.7 kb, 1.57 kb, or 2.1 kb regions of HIV pol. The unique PCR primers hybridize to highly conserved regions of pot. According to certain embodiments, the PCR application employs a hot start enzyme, such as AmpliTaq Gold. The novel HIV pol amplification primers are:

0.7 kb primers—
GGACTGTCAATGACATACAGAAGTTAGTGG (SEQ ID NO:3), and
GGTTAAAATCACTAGCCATTGCTCTCC (SEQ ID NO:4);

1.57 kb primers—GGAAAAGGGCTGTTGGAATGTG (SEQ ID NO:1), and
GGCTCTTGATAAATTTGATATGTCCATTG (SEQ ID NO:2), 2.1 kb primers—
CTCATGTTCATCTTGGGCCTTATCTATTC (SEQ ID NO:13), and either
GCCAGGGAATTTTCTTCAGAGCAG (SEQ ID NO:12), or
GGCCAGGGAATTTTCTTCAGAGC (SEQ ID NO:14).

According to certain embodiments, sequencing procedures can employ one or more novel sequencing primers specific for the amplified HIV pol fragments. The novel HIV pol sequencing primers are:

AGCCAACAGCCCCACCAG (SEQ ID NO:5),
CCATCCCTGTGGAAGCACATTG (SEQ ID NO:6),
GTTAAACAATGGCCATTGACAGAAGA (SEQ ID NO:7),
GGAACTGTATCCTTTAGCTTCCC (SEQ ID NO:8),
AATGCATATTGTGAGTCTG (SEQ ID NO:9),
GAAGAAGCAGAGCTAGAACTGGCAG (SEQ ID NO:10), and
AAGAAGCAGAGCTAGAACTGGCAGA (SEQ ID NO:11).

The following sequencing primers are also included in sequencing reactions, where appropriate:

GGGCCATCCATTCCTGGC (SEQ ID NO:15),
TGGAAAGGATCACCAGCAATATTCCA (SEQ ID NO:16), and
CTGTATTTCTGCTATTAAGTCTTTTGATG (SEQ ID NO:17).

To sequence the 0.7 kb HIV pol region one can use the primers:
AATGCATATTGTGAGTCTG (SEQ ID NO:9), and either
GAAGAAGCAGAGCTAGAACTGGCAG (SEQ ID NO:10), or
AAGAAGCAGAGCTAGAACTGGCAGA (SEQ ID NO:11).

Because these latter two sequencing primers appear to work equally well and provide similar results they can be used interchangeably. To obtain the sequence of the 0.7 kb region, one of the two sequencing primers is added to an aliquot of the 0.7 kb amplified target sequences and the second sequencing primer is added to a separate aliquot and the sequencing reaction is completed as described. The sequencing results from these two separate sequencing experiments are then combined and analyzed to provide the sequence for the 0.7 kb region.

Seven sequencing primers can be used to sequence the 1.57 kb HIV pol region:
AGCCAACAGCCCCACCAG (SEQ ID NO: 5),
CCATCCCTGTGGAAGCACATTG (SEQ ID NO:6),
GTTAAACAATGGCCATTGACAGAAGA (SEQ ID NO:7),
GGAACTGTATCCTTTAGCTTCCC (SEQ ID NO:8),
GGGCCATCCATTCCTGGC (SEQ ID NO:15),
TGGAAAGGATCACCAGCAATATTCCA (SEQ ID NO:16), and
CTGTATTTCTGCTATTAAGTCTTTTGATG (SEQ ID NO:17).

The procedure is the same as for the 0.7 kb region except that seven separate sequencing reactions, one for each sequencing primer, are performed and the seven sets of sequencing data are combined for analysis.

To sequence the 2.1 kb region, both the 0.7 kb sequencing primers (SEQ ID NO:15, and 16 or 17) and the 1.57 kb sequencing primers (SEQ ID NO:5, 6, 7, 8, 9, 10 and 11) can be used in nine separate sequencing reactions. The resulting nine sets of sequencing data are combined for analysis.

According to certain embodiments of the sequencing procedure, the new dye-terminator chemistries (dRhodamine and Big-Dye) were employed in place of dye-labeled primers. The new dye chemistries allow for more even incorporation of nucleotides and a much improved signal to noise ratio over the rhodamine terminators. The new Big-Dye terminator (U.S. Pat. No. 5,800,996) was chosen over the dRhodamine terminators because of the increased signal strength and better signal to noise ratio. This allows for a faster throughput for sequencing with increased data quality.

In certain embodiments, the target nucleic acid sequences are automatically analyzed by software that was developed for assigning an HIV genotype. The software incorporates two new features in the basecalling function: using known features of the sequences as previously determined from a set of standards (Conrad et al., 1995) and using the base identified on the complimentary strand to confirm the basecall. The use of experienced basecalling algorithms dramatically reduces the need for manual editing. The assembly of the basecalling primary data into a contiguous sequence is performed in a batch-wise manner by the software. The software then compares the derived sequence to a known HIV reference and table of known resistance mutations for genotypic assignment. Positions are reported that either differ in assignment by each of the sequence segments, differ from the HIV "wild-type" reference, or are found in the table of sequence mutations known to be correlated with drug resistance. This system can be coupled with the use of a sequence database for higher level analysis and data management.

The following examples are intended to be purely exemplary of the invention and are not intended to be limiting.

WORKING EXAMPLES

The following protocols were used with the 0.7 kb, 1.57 kb and 2.1 kb regions of HIV pol. All method steps and reagents remained constant, including the primer concentration, except that the specific amplifying and sequencing primers varied based on the HIV pol region being analyzed.

Example 1

RNA Preparation

Plasma samples, either freshly obtained or thawed at room temperature were vortexed for 3–5 seconds at medium to low speed and then briefly centrifuged to collect the specimen in the bottom of the tube. One half ml aliquots of plasma were placed into 1.5 ml microfuge tubes with snap tops, transferred to a centrifuge pre-chilled to 4° C. (Heraeus 17RS, Biofuge 22 R, Biofuge 28RS or Beckman Centrifuge GS-15R or equivalent), and centrifuged for 1 hour at 21,000 to 25,000×g at 4° C. in a pre-chilled rotor. After centrifugation, the supernatant was carefully removed and discarded. The pellet was resuspended in 600 µl lysis buffer and vortexed for 3–5 seconds at medium to low speed followed by incubation at room temperature for 10 minutes.

To precipitate the viral RNA, 600 µl of room temperature 100% Isopropanol was added and the capped tube was vortexed for 5–10 seconds at medium to low speed. The tube was then centrifuged in a microcentrifuge at maximum speed (at least 12,500×g) for 15 minutes at room temperature. The resulting supernatant was removed and discarded. The tube was then recentrifuged for 5–10 seconds and the residual liquid was removed with a fine pipette tip. It is important to remove as much liquid as possible.

The pellet was washed using 1.0 ml 70% ethanol, pre-chilled to 4° C. The tube was vortexed for 3–5 seconds to resuspend the pellet, then centrifuged in a microcentrifuge at maximum speed (at least 12,500×g) for 5 minutes at room temperature. Again the resulting supernatant was removed and discarded and the tube centrifuged for an additional 5–10 seconds to allow the removal of the residual liquid. To minimize RNA degradation samples should be kept on ice unless otherwise noted.

The washed RNA was resuspended in specimen diluent (10 ng/ml polyrA in RNase-free water) using either 50 µl if the viral load is either known or expected to be less than 10,000 copies/ml or 100 µl if the viral load is greater than 10,000 copies/ml. The sample was vortexed at medium to low speed for 10 seconds then centrifuged for 5–10 seconds in a microcentrifuge to collect the liquid to the bottom of the tube. The purified RNA was then used immediately as the initial template in the following two-step RT-PCR or stored at −70° C.

Example 2

Two-step, One Tube RT-PCR

The RT and PCR procedures of the instant invention are performed in the same tube but in two different steps. First purified RNA, HIV-1 RT Buffer (6.25 µM random hexamers, dATP, dCTP, dGTP and dTTP, all at 2.5 mM, and 6.25 mM $MgCl_2$ in 25 mM Tris-50 mM KCl buffer, ph 8.2), RNase inhibitor (Perkin Elmer) and Maloney Murine Leukemia Virus (MMuLV) reverse transcriptase (Perkin Elmer) were incubated under conditions to allow cDNA synthesis from the purified RNA template, which results in the generation of HIV derived double-stranded nucleic acid template.

Then, PCR mix (0.34 µM of each specific PCR primer, dATP, dCTP, dGTP and dTTP, all at 0.093 mM, 253 mM $MgCl_2$, in 10 mM Tris-50 mM KCl buffer, pH 8.2) and the temperature-stable DNA polymerase AmpliTaq Gold (Perkin Elmer) was added to the HIV derived double-stranded nucleic acid template and thermal cycled to produce amplified target sequences.

The two-step RT-PCR procedure is carried out in 0.2 ml tubes. The RT reaction mixture containing 8 µl HIV-1 RT Buffer Mix, 1 µl RNase inhibitor (20 U/µl), 1 µl MMuLV reverse transcriptase (50 U/µl) and 10 µl of purified RNA were placed in tubes, transferred to a thermal cycler pre-heated to 42° C. and cycled as follows: 42° C. for 60 minutes, 99° C. for 5 minutes, and were held at 4° C. to synthesize HIV derived double-stranded nucleic acid templates. These templates were used immediately for PCR or stored at −20° C. or below until use.

To each tube was added 29.5 µl HIV PCR mix, including 0.5 µl of each of the 5' and 3' specific PCR primers (20 pmole/µl), and 0.5 µl AmpliTaq Gold (5 U/µl). The final volume for PCR is 50 µl. To amplify the target sequences, the tubes were placed in a thermal cycler (e.g., Perkin Elmer model 9600, 9700 or 2400) and cycled as follows:

One cycle of:

95° C. for 10 minutes 40 cycles of:

95° C. for 15 seconds

64° C. for 45 seconds

68° C. for 3 minutes

One cycle of:

72° C. for 10 minutes followed by a

4° C. soak.

The specific PCR primers were for the 0.7 kb region: GGACTGTCAATGACATACAGAAGTTAGTGG (SEQ ID NO:3), and GGTTAAAATCACTAGCCATTGCTCTCC (SEQ ID NO:4); for the 1.57 region: GGAAAAAGGGCT-GTTGGAAATGTG (SEQ ID NO:1) and GGCTCT-TGATAAATTTGATATGTCCATTG (SEQ ID NO:2); and for the 2.1 region: CTCATGTTCATCTTGGGCCTTATC-TATTC (SEQ ID NO:13) and either GCCAGG-GAATTTTCTTCAGAGCAG (SEQ ID NO:12) or GGC-CAGGGAATTTTCTTCAGAGC (SEQ ID NO:14).

Example 3

Purification and Analysis of the RT-PCR Product

The RT-PCR product was purified by electrophoresis on an agarose gel prior to analysis of the target sequences.

Two hundred microliters of sterile water and all of the RT-PCR product (50 µl) was pipetted onto the top of a Microcon 100 microconcentrator (Amicon) and the microconcentrator was sealed with the attached cap. The microconcentrator was centrifuged in a bench top centrifuge at 800–845×g (3000 rpm) for 15 minutes at room temperature. The sample reservoir was removed from the vial and it was placed upside down in a new vial, which was then centrifuged for 3 minutes at 800–845×g (3000 rpm) to transfer the concentrated amplified target sequences to the vial. To each sample of amplified target sequence was added 35 µl of sterile water and 5 µl were analyzed by electrophoresis on an agarose gel. The remaining concentrated template can be stored at −20° C. for several months.

The amplified target sequences were analyzed on 1% agarose gel (Seakem GTC) containing 0.5 µg/ml ethidium bromide. Five microliters of concentrated amplified target sequence in an equal volume of agarose gel loading buffer/ dye (40% sucrose w/v, bromphenol blue 0.25% w/v, xylene cyanole FF 0.25% w/., 0.1 M EDTA pH 8.0, 0.5% sodium lauryl sulfate) was loaded into a gel lane and electrophoresed. In an adjacent lane, 2 µl of a DNA mass ladder was included as a standard (Low DNA Mass Ladder, GibcoBRL; markers for DNA fragments of 2, 1.2, 0.8, 0.4, 0.2, and 0.1 kb in 10 mM Tris-HCl, pH 7.5, 1 mM EDTA, containing 200, 120, 80, 40, 20 and 10 ng DNA/4 µl, respectively). The amplified target sequences were electrophoresed at 10 V/cm for 45–60 minutes. Upon visualization under UV light, a band containing the amplified target sequence should be seen at 0.7, 1.57, or 2.1 kb, depending on the PCR primers used, provided that the starting material contained HIV.

If the intensity of the amplified target sequence band is between the intensities of the 1.2 kb and 0.8 kb standard bands, the amplified target sequence should be diluted with three parts sterile distilled deionized water for use in the sequencing reaction. If the intensity of the amplified target sequence band is less than that of the 1.2 kb and the 0.8 kb standard bands, dilute the amplified target sequence with an equal volume of sterile distilled deionized water. If the amplified target sequence band is less intense than the 0.8 kb standard band, there may not be sufficient amplified target for sequencing.

Example 4

Sequencing of the Amplified Target Sequence (RT-PCR Product)

Depending on the HIV pol region being analyzed, the amplified target sequences were sequenced in either 2, 7, or 9 separate sequencing reactions, each employing different sequencing primers. For sequencing the 0.7 kb HIV pol region amplified target sequences, the sequencing primers were:

AATGCATATTGTGAGTCTG (SEQ ID NO:9), and either

GAAGAAGCAGAGCTAGAACTGGCAG (SEQ ID NO:10), or

AAGAAGCAGAGCTAGAACTGGCAGA (SEQ ID NO:11).

For sequencing the 1.57 kb HIV pol region amplified target sequences, the sequencing primers were:

AGCCAACAGCCCCACCAG (SEQ ID NO:5),

GGGCCATCCATTCCTGGC (SEQ ID NO:15),

TGGAAAGGATCACCAGCAATATTCCA (SEQ ID NO:16),

CTGTATTTCTGCTATTAAGTCTTTTGATG (SEQ ID NO:17),

CCATCCCTGTGGAAGCACATTG (SEQ ID NO:6),

GTTAAACAATGGCCATTGACAGAAGA (SEQ ID NO:7), and

GGAACTGTATCCTTTAGCTTCCC (SEQ ID NO:8).

For sequencing the 2.1 kb HIV pol region amplified target sequences, nine sequencing primers were used, the seven 1.57 kb region sequencing primers and two of the 0.7 kb region sequencing primers (SEQ ID NO:9 and either SEQ ID NO:10 or SEQ ID NO:11).

Each of the sequencing primers were diluted in BigDye Terminator Ready Reaction Mix (AmpliTaq Karl 1000–1200 U/ml, rTTH pyrophosphate 125–150 U/ml, ddA BigDye Terminator 0.27 µM, ddC Big Dye Terminator 0.41 µM, ddG Big Dye Terminator 0.26 µM, ddT Big Dye Terminator 2.8 µM, dATP 250 µM, dCTP 250 µM, dITP 1250 µM, dUTP 250 µM in 200 mM Tris-HCl, pH 9.05 and 5 mM MgCl₂) to a concentration of 0.267 mM. Eight microliter aliquots of the diluted amplified target sequences were transferred into each of the two, seven or nine sequencing tubes (for the 0.7, 1.57 and 2.1 kb regions, respectively) and 12 µl of one of the two, seven or nine primer-BigDye Terminator Ready Reaction Mix is added to each of sequencing tubes. The sequencing tubes are centrifuged briefly in a microcentrifuge to collect the reagents at the bottom of the tube.

The sequencing reaction tubes are then thermal cycled in either a PE 9600, 9700, or 2400 thermal cycler as follows: 25 cycles of 96° C. for 10 seconds, 50° C. for 5 seconds and 60° C. for 4 minutes, followed by a 4° C. soak. The sequencing tubes should be removed from the thermal cycler within 2 hours and either processed or wrapped in foil and frozen immediately at −20° C.

For each reaction, a 1.5 ml microcentrifuge tube was prepared containing 2 µl 3M sodium acetate (NaOAc), pH 4 and 50 µl 95% ethanol and the entire 20 µl sequencing reaction was transferred to the tube. Each tube was then vortexed 3–5 seconds, placed on ice for 10 minutes and centrifuged at maximum speed 12500×g (15000 rpm) for 30 minutes in a table top centrifuge, to pellet the sequencing products. The supernatant was removed and discarded and the pellet was washed with 250 µl of cold 70% EtOH, vortexed for 5 seconds and centrifuged for 5 minutes in a table top microcentrifuge at maximum speed 12500×g (15000 rpm). The supernatant was removed and the pellet was briefly dried in a pre-heated 95° C. heat block for 1–2 minutes. These pellets can be stored at −20° C., for at least 6 months.

The sequence products were analyzed by resuspending each pellet with 5 µl of the loading buffer-formamide (1 part recrystallized formamide in 5 parts loading buffer-25 mg/l blue dextran, 10 mM EDTA), vortexing 3–5 seconds at medium speed, and centrifuging 3–5 seconds at high speed the samples to bring all the liquid to the bottom of the tube. The samples were heated at 95° C. for 2 minutes to denature the sequencing products and electrophoresed on a sequencing gel at 1500 V.

The sequencing gels were analyzed to determine the target sequences, which were then compared with the "wild-type" HIV pol gene sequence. All mutations detected were compared with known drug resistance mutations.

The amplification and sequencing methods were used with primers specific for the 1.57 kb region of HIV pol using plasma samples form patients known to be infected with HIV. In one example, PE505, a total of 118 nucleotide variations were identified in the 1.57 kb pol region, of which 6 correlated to known drug resistance mutations, 5 in the viral protease and one in RT.

The sequence of the 1.57 HIV pol region, for clinical sample PE 505 is shown below. At several nucleotides two bases were detected, indicating that this sample probably contained more than one HIV quasi-species.

```
CCTCARATCACTCTTTGGCAACGACCAMTAGTCACAATAAAGATAGGGGG

GCAATTAAAGGAAGCTTTATTAGATACAGGAGCAGATGATACAGTATTAG

AAGAAATGAATTTGCCAGGAAAATGGAAACCAAAAATGATAGGGGGAATT

GGAGGTTTTATCAAAGTAAGACAGTATGATCAGRTACTCATAGAAATCTG

TGGACATAAAGCTATAGGTACAGTATTARTAGGACCTACACCTGTCAACA

TAATTGGAAGAAATCTGTTGACTCAACTTGGGTGCACTTTAAATTTTCCT
```

-continued

ATTAGTCCTATTGAAACTGTACCAGTAAAATTAAAGCCAGGAATGGATGG

CCCAAAAGTTAAACAATGGCCATTGACAGAAGAAAAAATAAAAGCATTAG

TAGAAATTTGTACAGAAATGGAAAAGGAAGGGAAAATTTCAAAAATTGGA

CCTGAAAATCCATACAATACTCCAGTATTTGCCATAAAGAAAAAAGACAG

TACTAGATGGAGAAAATTAGTAGATTTCAGAGAACTTAATAAGAGAACTC

AAGAYTTCTGGGAAGTTCAATTAGGAATACCACATCCTGCAGGGTTAAAA

AAGAAGAAATCAGTGACAGTACTGGATGTGGGTGATGCATATTTCTCAGT

TCCCTTAGATAAAGACTTCAGGAAGTATACTGCATTTACCATACCTAGTA

TAAACAATGAGACACCGGGGATTAGATATCAGTACAATGTGCTTCCACAG

GGATGGAAAGGATCACCAGCAATATTCCAGAGCAGCATGACAAAAATCTT

AGAGCCTTTTAGAAAACAAAATCCAGACATGGTTATCTATCAATACATGG

ATGATTTGTATGTAGGATCTGACTTAGAAATAGGGCAGCATAGAACAAAA

ATAGAGGAACTGAGAMAACATCTGTTGAAGTGGGGATTTACCACACCAGA

CAAAAAACATCAGAAGGAACCTCCATTCCTTTGGATGGGTTATGAACTCC

ATCCTGATAAATGGACAGTACAGCCTATAGAGCTGCCAGAAAAAGACAGC

TGGACTGTCAATGACATACAGAAGTTAGTGGGAAAATTGAATTGGGCAAG

TCAGATTTATCCAGGAATTAAGGTAAAGCAATTATGTAGACTCCTTAGGG

GAGCCAAAGCACTCACAGAAGTAATACCACTAACAAAGGAAGCAGAGATR

GAACTGGCAGAAAACAGGGAGATTCTAAAAGAGCCAGTACATGGAGTGTA

TTATGA

R-G or A residues were detected at this position
Y-C or residues were detected at this position
M-A or C residues were detected at this position References 1) Brown, A. J. L., and Richman, D. D. (1997). Gambling on the evolution of drug resistance. Nature Medicine 3, 268–271.
2) Coffin, J. M. (1995). HIV population dynamics in vivo: implications for genetic variation, pathogenesis and therapy. Science 267, 483–489.
3) Condra, J. H., Holder, D. J., Schleif, W. A., Blahy, O. M., Danovich, R. M., Gabryelski, L. J., Graham, D. J., Laird, D., Quintero, J. C., Rhodes, A., and Emini, E. A. (1996). Genetic correlates of in vivo viral resistance to indinavir, a human immunodeficiency virus type 1 protease inhibitor. Journal of Virology 70, 8270–8276.
4) Condra, J. H., Schleif, W. A., Blahy, O. M., Gabryelski, L. J., Graham, D. J., Quintero, J. C., Rhodes, A., Robbins, H. L., Roth, E., Shivaprakash, M., Titus, D., Yang, T., Teppler, H., Squires, K. E., Deutsch, P. J., and Emini, E. A. (1995). In vivo emergence of HIV-1 variants resistant to multiple protease inhibitors. Nature 374, 569–571.
5) Larder, B. A., Kellman, P., and Kemp, S. D. (1993). Convergent combination therapy can select viable multidrug-resistant HIV-1 in vitro. Nature 365, 451–453.
6) Mansky, L. M., and Temin, H. M. (1995). Lower in vivo mutation rate of human immunodeficiency virus-type 1 than that predicted from the fidelity of purified reverse transcriptase. Journal of Virology 69, 5087–5094.
7) Molla, A., Korneyeva, M., Gao, Q., Sudthida, V., Schipper, P. J., Mo, H. M., Markowitz, M., Chernyavskiy, T., Niu, P., Lyons, N., Hsu, A., Granneman, R., Ho, D. D., Boucher, C. A. B., Leonard, J. M., Norbeck, D. W., and Kempf, D. J. (1996). Ordered accumulation of mutations in HIV protease confers resistance to ritonavir. Nature Medicine 2, 760–766.
8) Seillier-Moiseiwitsch, F., Margolin, B. H., and Swanstrom, R. (1994). Genetic variability of the human immunodeficiency virus: statistical and biological issues. Annu. Rev. Genet. 28, 559–596.
9) Wain-Hobson, S. (1993). The fastest genome evolution ever described: HIV variation in situ. Current Opinions in Genetic Development 3, 878–883.
10) Mayers, D. (1998). Drug-resistant HIV-1, the virus strikes back. J. Amer. Med. Assn. 297, 2000–02.
11) Hirsch, M., Conway, B., D'Aquila, R., Johnson, V., Brun-Vezinet, F., Clotet, B., Demeter, L., Hammere, S., Jacobsen, D., Kuritzkes, D., Loveday, C., Mellors, J., Vella, S., and Richman, D. (1998). Antiviral drug resistance testing in adults with HIV infection. J. Amer. Med. Assn. 297, 1984–91.
12) Wainberg, M. and Friedland, G. (1998). Public health implications of antiretroviral therapy and HIV drug resistance. J. Amer. Med. Assn. 297, 1977–83.
13) Conrad M. P., C. L. Brown, R. B. Chadwick, L. A. Johnston-Dow, M. C. McGinnis, E. H. Rozemuller, M. G. J. Tilanus, and M. Kronick (1995). Pattern matchin software achieves more reliable automated HLA sequencing-based typing. Abstract. Human Immunology Vol. 4, Supp.1, p. 151.

What is claimed is:

1. A method of identifying mutations associated with drug resistance in an HIV quasi-species comprising:
   a) preparing nucleic acid from a human body fluid sample;
   b) preparing double stranded nucleic acid template from HIV RNA in the nucleic acid;
   c) amplifying a region of HIV pol from the double stranded nucleic acid template to obtain an amplification product;
   d) sequencing the amplification product using one or more specific sequencing primers; and
   e) identifying mutations associated with drug resistance in an HIV quasi-species.

2. The method of claim 1, wherein the region of HIV pol comprises the entire coding region of protease and reverse transcriptase.

3. The method of claim 2, wherein the amplifying of region of HIV pol comprises using a first primer comprising SEQ ID NO:13 and a second primer comprising SEQ ID NO:12 or SEQ ID NO:14.

4. The method of claim 2, wherein the sequencing of the amplification product comprises using one or more primers selected from SEQ ID NOs:5–11 and 15–17.

5. The method of claim 1, wherein the sequencing of the amplification product comprises using more than one specific sequencing primer.

6. The method of claim 1, wherein the preparing of nucleic acid from a human body fluid sample comprises pelleting virion by centrifuging the human body fluid sample.

7. The method of claim 1, wherein the preparing of the double stranded nucleic acid template comprises reverse transcribing the HIV RNA.

8. The method of claim 7, wherein the preparing of the double stranded nucleic acid template and the amplifying of the region of HIV pol from the double stranded nucleic acid template take place in the same reaction vessel.

* * * * *

SEQUENCE LISTING

<160> NUMBER OF SEQ ID NOS: 18

<210> SEQ ID NO 1
<211> LENGTH: 23
<212> TYPE: DNA
<213> ORGANISM: HIV

<400> SEQUENCE: 1 ggaaagggc tgttggaaat gtg                    23

<210> SEQ ID NO 2
<211> LENGTH: 29
<212> TYPE: DNA

```
<213> ORGANISM: HIV

<400> SEQUENCE: 2
ggctcttgat aaatttgata tgtccattg                              29

<210> SEQ ID NO 3
<211> LENGTH: 30
<212> TYPE: DNA
<213> ORGANISM: HIV

<400> SEQUENCE: 3
ggactgtcaa tgacatacag aagttagtgg                             30

<210> SEQ ID NO 4
<211> LENGTH: 27
<212> TYPE: DNA
<213> ORGANISM: HIV

<400> SEQUENCE: 4
ggttaaaatc actagccatt gctctcc                                27

<210> SEQ ID NO 5
<211> LENGTH: 18
<212> TYPE: DNA
<213> ORGANISM: HIV

<400> SEQUENCE: 5
agccaacagc cccaccag                                          18

<210> SEQ ID NO 6
<211> LENGTH: 22
<212> TYPE: DNA
<213> ORGANISM: HIV

<400> SEQUENCE: 6
ccatccctgt ggaagcacat tg                                     22

<210> SEQ ID NO 7
<211> LENGTH: 26
<212> TYPE: DNA
<213> ORGANISM: HIV

<400> SEQUENCE: 7
gttaaacaat ggccattgac agaaga                                 26

<210> SEQ ID NO 8
<211> LENGTH: 23
<212> TYPE: DNA
<213> ORGANISM: HIV

<400> SEQUENCE: 8
ggaactgtat cctttagctt ccc                                    23

<210> SEQ ID NO 9
<211> LENGTH: 19
<212> TYPE: DNA
<213> ORGANISM: HIV

<400> SEQUENCE: 9
aatgcatatt gtgagtctg                                         19

<210> SEQ ID NO 10
<211> LENGTH: 25
```

```
<212> TYPE: DNA
<213> ORGANISM: HIV

<400> SEQUENCE: 10
gaagaagcag agctagaact ggcag                                25

<210> SEQ ID NO 11
<211> LENGTH: 25
<212> TYPE: DNA
<213> ORGANISM: HIV

<400> SEQUENCE: 11
aagaagcaga gctagaactg gcaga                                25

<210> SEQ ID NO 12
<211> LENGTH: 24
<212> TYPE: DNA
<213> ORGANISM: HIV

<400> SEQUENCE: 12
gccagggaat tttcttcaga gcag                                 24

<210> SEQ ID NO 13
<211> LENGTH: 29
<212> TYPE: DNA
<213> ORGANISM: HIV

<400> SEQUENCE: 13
ctcatgttca tcttgggcct tatctattc                            29

<210> SEQ ID NO 14
<211> LENGTH: 23
<212> TYPE: DNA
<213> ORGANISM: HIV

<400> SEQUENCE: 14
ggccagggaa ttttcttcag agc                                  23

<210> SEQ ID NO 15
<211> LENGTH: 18
<212> TYPE: DNA
<213> ORGANISM: HIV

<400> SEQUENCE: 15
gggccatcca ttcctggc                                        18

<210> SEQ ID NO 16
<211> LENGTH: 26
<212> TYPE: DNA
<213> ORGANISM: HIV

<400> SEQUENCE: 16
tggaaaggat caccagcaat attcca                               26

<210> SEQ ID NO 17
<211> LENGTH: 29
<212> TYPE: DNA
<213> ORGANISM: HIV

<400> SEQUENCE: 17
ctgtatttct gctattaagt cttttgatg                            29

<210> SEQ ID NO 18
```

-continued

```
<211> LENGTH: 1256
<212> TYPE: DNA
<213> ORGANISM: HIV

<400> SEQUENCE: 18
cctcaratca ctctttggca acgaccamta gtcacaataa agatagggg gcaattaaag      60 gaagctttat tagatacagg agcagatgat acagtattag aagaaatgaa tttgccagga    120
aaatggaaac caaaaatgat aggggaatt ggaggttta tcaaagtaag acagtatgat    180
cagrtactca tagaaatctg tggacataaa gctataggta cagtattart aggacctaca    240
cctgtcaaca taattggaag aaatctgttg actcaacttg ggtgcacttt aaatttcct    300 attagtccta ttgaaactgt accagtaaaa ttaaagccag gaatggatgg cccaaaagtt    360
aaacaatggc cattgacaga agaaaaaata aaagcattag tagaaatttg tacagaaatg    420
gaaaaggaag ggaaaatttc aaaaattgga cctgaaaatc catacaatac tccagtattt    480
gccataaaga aaaagacag tactagatgg agaaaattag tagatttcag agaacttaat    540
aagagaactc aagayttctg ggaagttcaa ttaggaatac cacatcctgc agggttaaaa    600
aagaagaaat cagtgacagt actggatgtg ggtgatgcat atttctcagt tcccttagat    660
aaagacttca ggaagtatac tgcatttacc atacctagta taaacaatga gacaccgggg    720
attagatatc agtacaatgt gcttccacag ggatggaaag gatcaccagc aatattccag    780
agcagcatga caaaaatctt agagccttt agaaaacaaa atccagacat ggttatctat    840
caatacatgg atgatttgta tgtaggatct gacttagaaa tagggcagca tagaacaaaa    900
atagaggaac tgagamaaca tctgttgaag tggggattta ccacaccaga caaaaaacat    960
cagaaggaac ctccattcct ttggatgggt tatgaactcc atcctgataa atggacagta   1020
cagcctatag agctgccaga aaaagacagc tggactgtca atgacataca gaagttagtg   1080
ggaaaattga attgggcaag tcagatttat ccaggaatta aggtaaagca attatgtaga   1140
ctccttaggg gagccaaagc actcacagaa gtaataccac taacaaagga agcagagatr   1200
gaactggcag aaaacaggga gattctaaaa gagccagtac atggagtgta ttatga       1256
```